(12) United States Patent
Suner et al.

(10) Patent No.: US 7,033,784 B1
(45) Date of Patent: Apr. 25, 2006

(54) METHOD OF PRODUCING AN ERYTHROID CELL WHICH IS UNDIFFERENTIATED YET CAPABLE OF EXPRESSING A HETEROLOGOUS PROTEIN

(75) Inventors: Marie-Marthe Suner, Berkshire (GB); John Windass, Berkshire (GB); Fergus Gerard Paul Earley, Berkshire (GB); Stuart John Dunbar, Berkshire (GB); Judith Lesley Blythe, Berkshire (GB)

(73) Assignee: Syngenta Limited, (GB)

( * ) Notice: Subject to any disclaimer, the term of this patent is extended or adjusted under 35 U.S.C. 154(b) by 0 days.

(21) Appl. No.: 10/009,231

(22) PCT Filed: Apr. 5, 2000

(86) PCT No.: PCT/GB00/01702

§ 371 (c)(1),
(2), (4) Date: Apr. 9, 2002

(87) PCT Pub. No.: WO00/68362

PCT Pub. Date: Nov. 16, 2000

(30) Foreign Application Priority Data

May 7, 1999 (GB) .................................. 9910664

(51) Int. Cl.
| C12Q 1/68 | (2006.01) |
| G01N 33/53 | (2006.01) |
| G01N 33/566 | (2006.01) |
| C12N 5/00 | (2006.01) |
| C12N 15/09 | (2006.01) |

(52) U.S. Cl. .................... 435/69.1; 435/6; 435/7.1; 435/7.25; 435/320.1; 435/325

(58) Field of Classification Search .................. 435/4, 435/6, 7.1, 70.1, 325, 377, 320.1
See application file for complete search history.

(56) References Cited

U.S. PATENT DOCUMENTS 5,538,885 A * 7/1996 Hollis et al. ................. 435/355
5,631,162 A * 5/1997 LeBoulch et al. ....... 435/320.1

FOREIGN PATENT DOCUMENTS

| GB | 2251622 | 7/1992 |
| WO | WO 92/11380 | 7/1992 |
| WO | WO 98/35020 | 8/1998 |

OTHER PUBLICATIONS

Poels et al. Functional expression of a locus tyramine receptor in murine erythroleukaemia cells. Insect Molec Biol 10(6): 541-548, 2001.*
Needham et al. Further development of the locus control region/murine erythroleukemia expression system: high level expression and characterization of recombinant human calcitonin receptor. Protein Expr Purif. 6(2):124-131, 1995.*
Amar et al. Expression of a bovine GABAA receptor alpha1-subunit cDNA in murine erythroleukaemia cells.□□J Recept Signal Transduct Res. 15(1-4):71-79, 1995.*
Vannucchi et al. Constitutive and inducible expression of megakaryocyte-specific genes in Friend erythroleukaemia cells.□□Br J Haematol. 99(3):500-508, 1997.*
Davies et al. The application of the human beta-globin gene locus control region and murine erthroleukemia cell system to the expression and pharmacological characterization of human endothelin receptor subtypes.J Pharmacol Toxi Methods.33(3)153-158, 1995.*
Deisseroth et al. Human alpha-globin gene expression following chromosomal dependent gene transfer into mouse erythroleukemia cells. Cell 15(1):55-63, 1978.*
Uings et al. Cell receptors and cell signalling. J Clin Pathol Molec Pathol 53: 295-299, 2000.*
Rozengurt, E. Signal transduction pathways in the mitogenic response to G protein-coupled neuropeptide receptor agonists. J Cell Physiol. 177(4):507-517, 1998.*
Garcia-Alonso M. et al. "Stable Functional Expression of the Neuronal Nicotinic Acetylcholine Receptor α3β4 in MEL (Murine Erythroleukemia) Cells: A Novel Expression System for Ligand Gated Ion Channels", *Society for Neuroscience Abstracts*, vol. 22, p. 1526 (1996).
Needham M. et al. "LCR/MEL: A versatile system for high-level expression of heterologous proteins in erythroid cells", *Nucleic Acids Research*, vol. 20 No. 5, pp. 997-1003 (1992).
Migliaccio A.R. et al., "Molecular control of erythroid differentiation", *International Journal of Hematology*, vol. 64, pp. 1-29 (1996).

* cited by examiner

*Primary Examiner*—Elizabeth Kemmerer
*Assistant Examiner*—Bridget E. Bunner
(74) *Attorney, Agent, or Firm*—Mary Kakefuda

(57) ABSTRACT

A method of producing an erythroid cell which is substantially undifferentiated but which is capable of expressing a heterologous protein under the control of a globin promoter thereof, which method comprises maintaining growing uninduced erythroid cells in culture for sufficient period of time that the protein is expressed, and isolating a subclone which expresses said protein. Erythroid cells produced by the method, and methods of detecting the interaction of an insect G-protein coupled receptor with an endogenous signaling cascade of erythroid cells are also described and claimed.

9 Claims, 10 Drawing Sheets

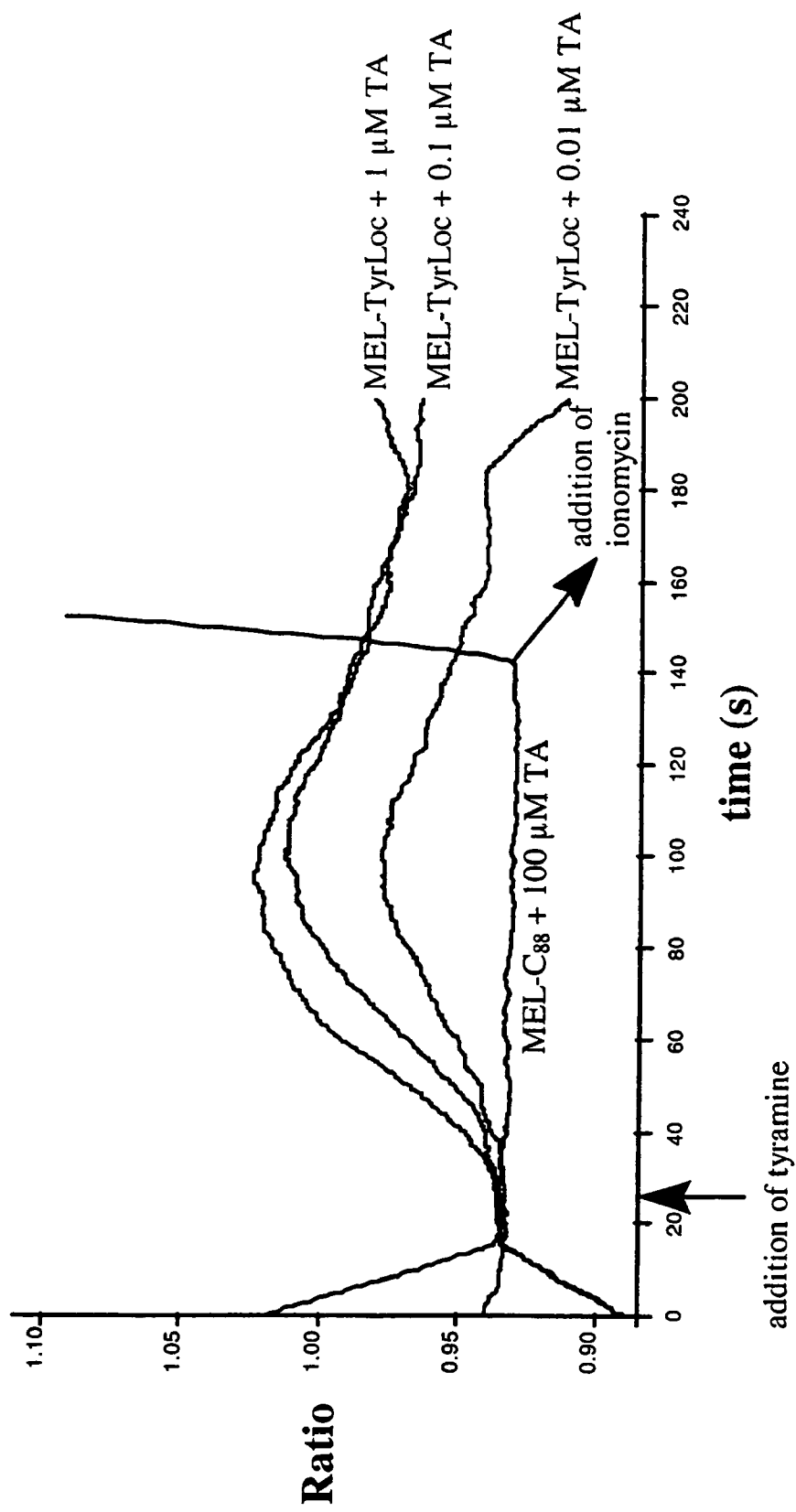

SEQUENCE LISTING

<160> NUMBER OF SEQ ID NOS: 4

<210> SEQ ID NO 1
<211> LENGTH: 48
<212> TYPE: DNA
<213> ORGANISM: Artificial Sequence
<220> FEATURE:
<223> OTHER INFORMATION: PCR Primer TryLocF2

<400> SEQUENCE: 1
ttttaagctt gaattcagat ctgccaccat gaacgggtct tcggctgc      48

<210> SEQ ID NO 2
<211> LENGTH: 46
<212> TYPE: DNA
<213> ORGANISM: Artificial Sequence
<220> FEATURE:
<223> OTHER INFORMATION: PCR Primer TryLocRev

<400> SEQUENCE: 2
ttttggatcc gcggccgcgt cgactcatgt cttgaagtgg agcagc      46

<210> SEQ ID NO 3

```
<211> LENGTH: 45
<212> TYPE: DNA
<213> ORGANISM: Artificial Sequence
<220> FEATURE:
<223> OTHER INFORMATION: PCR Primer DopD1/5FR

<400> SEQUENCE: 3
ttttaagctt agatctgcca ccatgtacac accaacaccc atttg        45

<210> SEQ ID NO 4
<211> LENGTH: 39
<212> TYPE: DNA
<213> ORGANISM: Artificial Sequence
<220> FEATURE:
<223> OTHER INFORMATION: PCR Primer DopD1/5RV

<400> SEQUENCE: 4
ttttgcggcc gcgtcgactc aaatcgcaga cacctgctc               39
```

METHOD OF PRODUCING AN ERYTHROID CELL WHICH IS UNDIFFERENTIATED YET CAPABLE OF EXPRESSING A HETEROLOGOUS PROTEIN

The present invention relates to cells and particularly erythroid cells, to methods of producing them and their use in assays, as well as to vectors useful in the methods.

In animal cell expression, the ideal has always been to have a system capable of reproducible, high level, stable expression of the proteins of interest. The LCR/MEL expression system (Locus Control Region/Murine Erythroleukemia cells) complies with this demand as previously demonstrated by Amar et al., (1995) J. Recept. Signal Tr. R. 15 71–79; Egerton et al, (1995) J. Mol. Endocrinol. 14 179–189; Needham et al, (1992) Nucleic Acids Res. 20 997–1003, Needham et al., (1995) Protein Expres. Purif. 6 124–131; Newton et al., (1994) Protein Expres. Purif. 5 449–457 and Shelton et al., (1993) Receptor. Channel. 1 25–37.

MEL cells are erythroid progenitor, robust, semi-adherent cells with a doubling time of only 10 to 16 hours, which are derived from spleens of susceptible mice infected with the Friend Virus Complex (Friend C (1957) J. Exp. Med. 105 307–318). They are continuously dividing cells, arrested at the proerythroblast stage. Changes similar to normal red blood cell maturation can be induced with a variety of chemical agents, including polar-planar compounds like dimethyl sulfoxide (DMSO). This terminal differentiation causes an increase of globin gene expression which can result in α and β globin comprising up to 25% of the total cell protein. The globin LCR enhancer is responsible for high levels of erythroid cell specific expression of globin proteins.

The human globin LCR has been utilised in the LCR/MEL system, alongside a human β-globin promoter in cis, to drive integration site position independent expression of cDNA and genomic sequences (Needham et al., 1995 supra.). The globin LCR confers integration site independent expression on stably transfected genes which are linked in cis (Blom von Assendelft et al. (1989) Cell 56 969–977; Talbot et al. (1989) Nature 338 352–355). The human β-globin promoter and parts of the β-globin gene provide mRNA processing and maturation signals, give stability to the final mRNA and confer high expression levels in induced cells (Needham et al., 1992 supra).

The LCR/MEL system has already been used to express a variety of proteins. Stable expression of electrophysiologically functional mammalian homo- and hetero-multimeric ion channel proteins has been obtained in MEL cells (Amar et al., 1995 supra.; Shelton et al., 1993 supra. and Monica Garcia-Alonso (1997) "Evaluation of the potential of Murine Erythroleukemia (MEL) cells as an expression system for nicotinic acetylcholine receptors" (Ph.D. thesis Reading University UK)). The LCR/MEL system is capable of producing functional secreted proteins (Needham et al., 1992 supra.; Newton et al., 1994 supra.). It has also been shown to produce very high levels of mammalian G-protein coupled receptors (sometimes known as seven-transmembrane helix receptors or 7TMR) as a source for ligand binding experiments (Egerton et al., 1995 supra.; Needham et al., 1995 supra.).

UK Patent No. 2251622 describes and claims expressions systems, including those based upon MEL cells, for the expression of heterologous polypeptides, in particular human proteins such as human growth hormone.

All of the previous examples of expression from MEL cells were of proteins of mammalian origin. High level expression of the genes was only seen after the recombinant MEL cell differentiation had been induced, although some background expression of a heterologous reporter gene (CAT) under the influence of an α-globin promoter in uninduced MEL cells has been described (Pondel et al., Nucl. Acids Res. 20, 2, 237–243).

There are several approaches to achieve stable, heterologous expression of G protein-coupled receptors in animal cells (Vanden Broeck, 1996, Int. Rev. Cytol. 164, 189–268). The majority of examples have come from mammalian systems. In conventional mammalian cloning systems, it can prove to be labour intensive to produce stable recombinant cell lines reliably expressing large amounts of receptor as well as to produce large numbers of recombinant cells.

The LCR/MEL cell expression system resolves these problems, as it is capable of reproducible, high level, stable expression of receptors as well as being a robust semi-adherent cell line (Needham et al., 1992). However, with the conventional LCR/MEL system, heterologous protein expression only occurs at high levels after induction of differentiation of the cells into mature red blood cells. Unfortunately, this differentiation frequently leads to the loss of functionality of the signalling cascades usually linked to G protein-coupled receptors. This means that the existing LCR/MEL system is ideal for ligand binding assays on recombinant MEL cells, but cannot be used in functional assays ($Ca^{2+}$, IP3 or cAMP assays). As a consequence, functional assays with G-protein coupled receptors have to be performed in other systems.

According to the present invention there is provided the use of an erythroid cell which is substantially undifferentiated but which is capable of expressing a heterologous protein under the control of a globin promoter thereof, in an assay in which said protein interacts with an endogenous signalling cascade of said cell and said interaction is detected.

Such assays are functional assays. Ligand binding assays may also be effected if the cells are induced prior to assay.

Suitable erythroid cells are murine erythroleukaemia (MEL) cells, rat erythroleukaemia cells (REL) and human erythroleukaemia cells (HEL), but are preferably murine erythroleukaemia cells.

Particular globin promoters which control expression of proteins in the cells of the invention are the β-globin promoters, such as human β-globin promoters.

In a further aspect, the invention provides an erythoid cell which is substantially undifferentiated but which is capable of expressing proteins under the control of a globin promoter thereof at levels which allow use as described above.

Cells in accordance with the invention can be obtained by culture of uninduced erythroid cells for a sufficient period of time, usually over a period of a few months, until they become "leaky" in the sense that protein under the control of globin promoters are expressed.

Leakiness in cells can be detected by routine methods. For example, the cells can be screened for mRNA levels using for example Northern blotting techniques. Detection of protein mRNA, for example β-globin mRNA would be sufficient to indicate that the cells were in the correct stage.

Alternatively, the cells can be transformed with a reporter or marker gene which is placed under the control of a globin promoter, preferably a β-globin promoter, and detecting expression of the marker gene in uninduced cells. Suitable reporter or marker genes for use in this process are well known in the art and include for instance the β-galactosidase gene (β-Gal).

In a further alternative, it may be possible to determine that the cells are in the correct state because they are beginning to change colour, by taking on a pinkish hue, indicating that a progression to red differentiated erythroid cells has begun. This may be detected either spectrometrically or by eye.

A yet further alternative is to detect expressed proteins themselves, for example using a conventional antibody type assay which may be either a direct or competitive assay. Examples of suitable proteins which may be detected include globins. Means of carrying out such assays are well known in the literature and include the use of labelled antibodies, for example radiolabelled or fluorescent antibodies, as well as enzyme-linked immunoassays (ELISAs).

A particular type of cell which can form cells of the invention are subclones of the MEL C-88 cell line, an example of which was deposited at the European Collection of Cell Cultures (ECACC), Health Protection Agency, Porton Down, Salisbury, Wiltshire SP4 0JG. United Kingdom under the Accession number 99012801, deposited on 28 Jan. 1999. This clone has been designated "MEL-C88L".

Cell lines of this type can be used in functional assays as illustrated hereinafter, since the cells retain nucleii which are lost or otherwise functionally silenced on terminal erythroid differentiation. Thus use can be made of the signalling pathways in the cell, such as those in which G-proteins are involved, where for example, globin promoters can drive the expression of heterologous proteins which normally functionally interact with a G-protein, in particular G-protein coupled receptor molecules (GPCR). These receptor molecules may be of mammalian or non-mammalian origin and in particular are insect receptors such as the *Locusta migratoria* tyramine receptor (TyrLoc), or other receptors such as dopamine, octopamine, serotonin, or acetylcholine receptors such as muscarinic acetylcholine receptors.

In a further aspect, the invention provides a method for determining the interaction between a receptor protein and a potential agonist or antagonist therefor, said method comprising incubating a cell as defined above which has been transformed so that it expresses said receptor protein as a G-protein coupled receptor, either (I) in (a) the presence and (b) the absence of said potential agonist; and/or (II) in the presence of a known agonist and (a) the presence or (b) the absence of said potential antagonist; and measuring and comparing G-protein induced signals in cells of (Ia) and (Ib) and/or (IIa) and (IIb).

The G-protein coupled receptor signal is induced in the presence of ligands for that receptor. In such a case, the G-protein coupled receptor which is expressed in MEL C88L cells, interacts with the G-protein and triggers a signalling cascade which may either increase or decrease the concentrations of various detectable components within the cell. Mechanisms by which these signalling cascades may operate are illustrated in the literature, for example, S. Klostermann et al., Perspectives in Neurobiology, (1996) 4, 237–252 and M. A. D. Fazia, FEBS Letters 410 (1997) 22–24.

The levels of these signals may be indicative of agonist or antagonist activity. This is particularly applicable if other possible target sites in the signalling cascade on which the compound may act have been eliminated, for example by carrying out specific assays for the other possible target sites, carrying out assays on untransformed cells, and/or using electrophysiological assays or studies on receptors or receptor preparations. Whether these changes are the result of the presence of the specific candidate agonist or antagonist can then be established by observing the difference between the signals generated by the cell line expressing the receptor protein of interest and the untransformed progenitor cell line i.e. cell lines differing only in the presence/absence of the target receptor. Where an elevated or heightened G-protein coupled receptor induced signal results in an elevation of the amounts of a particular downstream component in the signalling cascade, the signal generated by (Ia) will be greater than that generated by (Ib) if the potential agonist is effective. Under similar circumstances, the signal from step IIa above will be lower than that obtained in IIb if the potential antagonist is effective. Conversely, if an elevated G-protein coupled receptor induced signal results in a decrease in the concentration of a particular downstream component in the signalling cascade, application of a potential agonist would result in a reduction of the levels of that component. This can often only be detected by amplifying the signal using a chemical which artificially stimulates the level of the component e.g. forskolin. Sometimes, a further chemical which artificially inhibits an enzyme in the pathway is also added, as this again contributes to an increase in the level of the component. An example of such a further chemical is 3-isobutyl-1-methylxanthine (IBMX). Step (Ia) will then be lower than step (Ib). Where an antagonist in being assayed, the results of step (IIa) will be greater than (IIb), but can only be detected in the presence of forskolin.

In one embodiment, the G-protein coupled receptor induced signal is monitored by measuring the free calcium ion concentration of the cells. This can be done using known techniques, for example utilising a fluorescent indicator, such as fura-2 which binds free calcium ions, and whose fluorescent signal alters depending upon whether it is bound to calcium ions or free.

In an alternative embodiment, the G-protein coupled receptor induced signal is monitored by measuring the cyclicAMP (cAMP) levels within the cell, which may be increased or decreased, depending upon the nature of the G-protein coupled receptor. The G-protein coupled receptor induced signal activates the G-protein which interacts with adenylate cyclase enzyme either to increase or decrease the levels of cAMP in the cell. cAMP can be extracted from the cells and quantified using commercially available kits such as scintillation proximity assay (SPA) kits available from Amersham International (UK).

The calcium signalling mechanism is similar in that the concentration of calcium ions found in cells changes (either increases or decreases) as a result of G-protein induced signal.

In yet a further embodiment, the cells may be further transformed with a reporter or marker gene, such as β-galactosidase, expression of which is regulated by the G-protein coupled receptor signalling cascade. Changes in the signal will then be apparent by detecting the expression levels of the marker gene.

If necessary, where the G-protein coupled receptor induced signal results in a decrease in the level of the measured cellular component, the changes in the signal can be amplified by adding chemicals which either stimulate or inhibit components in the signalling pathway so resulting in an increase of the detectable chemical in the cell. For example, forskolin (FSK) is known to artificially stimulate cAMP levels in a cell by directly activating adenylate cyclase. 3-Isobutyl-1-methylxanthine (IBMX) is known to artificially increase cAMP levels in the cell by inhibiting cAMP phosphodiesterase. Hence when the G-protein coupled receptor signal results in a decrease in cAMP levels, this decrease may appear more clearly if the agonist, with or without antagonist, is added in the presence of forskolin and optionally also IBMX. An effective agonist would be expected to reduce the amount of cAMP as compared to the forskolin, or the forskolin and IBMX alone. The presence of an effective antagonist would mean that the levels of cAMP would be higher than the test (IIb), in the absence of the antagonist.

In such cases, a further assay, in the presence of forskolin, forskolin and IBMX or other artificial stimulants alone may be of assistance in the determining the levels of efficacy of the agonist or antagonist, and or in assessing the relative efficacies of various potential agonists and antagonists.

In all cases, cells of the invention are first transformed so that they express the G-protein coupled receptor of interest and clones which provide a good G-protein coupled receptor induced signal can be selected by testing each clone by adding varying amounts of the known receptor ligand, and if necessary, a chemical which stimulates the detectable cellular component (as discussed above). Clones which provide the most clearly distinguishable signals as between (Ia) and (Ib) and/or (IIa) and (IIb) above are selected for use in assays.

Cells of the invention can be used to express heterologous proteins, including human proteins. In particular however, the applicants have found that they are useful in the expression of non-mammalian and especially insect proteins.

To date, MEL cells giving a significant background level of G-protein coupled receptor expression in the absence of inducers such as dimethylsulphoxide (DMSO), have been used in a number of independent transformation experiments. In each case, even where a small number of transformed clones, for example $\geq 3$, were analysed, isolates showing both efficient inducible but low level "leaky" expression of the introduced heterologous genes were identified.

The applicants have, for the first time, expressed an insect G-protein coupled receptor in the LCR/MEL system: the locust tyramine receptor, TyrLoc. This receptor was previously expressed in stably transfected *Drosophila* S2 cells (Vanden Broeck et al. (1995) J. Neurochem. 64 2387–2395). The present results with the MEL-TyrLoc cells indicate that the pharmacology of the receptor expressed in these mammalian cells is similar to that in S2-TyrLoc cells. Both $Ca^{2+}$ and cAMP measurements demonstrate that there is a very efficient coupling of the expressed insect receptor to the endogenous, mammalian G proteins. This observation indicates that the use of this novel MEL expression system should not necessarily be restricted to the characterization and functional analysis of mammalian receptor proteins. Moreover, the ability of the LCR/β-globin promoter combination to confer high levels of expression, in a reproducible and position independent manner, is not affected in this MEL C88L cell clone.

This was shown by the fact that the monophenolic amine, tyramine (TA) is a much better agonist than octopamine (OA). It activates this receptor at concentrations which are 3–4 orders of magnitude lower than OA. Also, yohimbine proved to be a better receptor antagonist than chlorpromazine and mianserin.

These results clearly confirm the ligand binding data and the attenuating effect of TA on forskolin stimulated cAMP production which were previously obtained with TyrLoc expressing S2 cells (Vanden Broeck et al., 1995 supra.). G protein-coupled receptors for phenolamines (TA and/or OA) have been identified in other insect species (*Drosophila melanogaster*: Arakawa et al. (1990) Neuron 2 343–354 and Saudou et al., (1990) EMBO J. 9 3611–3617; *Heliothis virescens*: Von Nickisch-Rosenegk et al., (1996) Insect Biochem. Molec. Biol. 26 817–827) and in the mollusc *Lymnea stagnalis* (Gerhardt C C et al., (1997) Mol. Pharmacol. 51 293–300). The *H. virescens* (K50Hel) and *L. stagnalis* (Lym-OA1) receptors are preferentially activated by OA, whereas the fruitfly receptor (Tyr/Oct-Dro) produces agonist-specific (TA versus OA) coupling to different second messenger systems when it is expressed in NIH 3T3 (Saudou et al., 1990 supra.), in CHO cells (Robb (1994) EMBO J. 13 1325–1330) or in *Xenopus* oocytes (Reale et al. (1997) Brain Res. 769 309–320).

Assays using the cells of the invention and methods in accordance with the invention have been shown to be effective in determining the relative strengths of receptor agonists and antagonists. Specifically, it has been found that the locust receptor TyrLoc is more sensitive to TA than OA as agonists for both cAMP inhibition and $Ca^{2+}$ stimulation in MEL-TyrLoc cells.

These assays are useful in investigations into the biological function of molecules. For example, it is known that TA is the biosynthetic precursor of OA and it is present in many parts of the locust nervous system. The results reported here also imply that TA might be a very important neuro-active substance and this idea is strongly supported by the discovery of separate activities, binding sites and uptake systems for tyramine and octopamine in the locust central nervous system (Roeder T (1994) Comp. Biochem. Physiol. 107C 1–12; Hiripi L et al., (1994) Brain Res. 633 119–126.; Downer et al., (1993) Neurochem. Res. 18 1245–1248).

After induction, this clone also differentiates along the erythroid pathway and as a result boosts the expression levels of heterologous TyrLoc receptor proteins at least three- to four-fold. As a consequence, when induced, this clone loses the functionality of its signal transduction pathway, but is now ideal for ligand binding assays.

Thus the invention further provides an assay for detecting binding between a protein and a potential binding partner therefore, said method comprising (a) transforming a cell as described above so that the protein is expressed under the control of a globin promoter, (b) detecting binding between said potential binding partner and the protein on the membrane of the cell. Optionally, the cells are induced after step (a) and prior to step (b), so as to obtain high levels of protein expression from fully differentiated cells.

Step (b) may be effected on whole cells, or on isolated membranes extracted from lysed cells. Suitably, the protein is a receptor and the potential binding partner is a ligand therefore. However, binding between other types of protein, such as naturally occuring proteins, antigens, immunoglobulins such as antibodies, and binding partners, in particular specific binding partners can be tested in this manner.

This work demonstrates that the MEL cell line can be an even more versatile system than previously thought. It may be used in a variety of situations, from functional (G-protein coupled receptor signalling cascade or ligand gated ion channels) to ligand binding assays, for both mammalian and insect, secreted or transmembrane proteins.

Vectors used in tranformation of the cell lines form a further aspect of the invention.

Preferably, a "parent" cell line is established for use in the assays described above. This is a cell line comprising cells of the invention which have been transformed such that they express a suitable reporter gene such as the LacZ gene, under the control of a response element which is susceptible to modulation by a signalling cascade used in the assay. An example of such a response element would be a cAMP response element (CRE). The reporter gene is suitably also under the control of a minimal promoter, for example a minimal globin promoter. Suitable enhancers may also be included in order to ensure good expression levels. A particular enhancer is the LCR enhancer described above. Suitably, the distance and/or orientation between the enhancer and the promoter is arranged such that good or optimal induction of expression of the reporter gene by an increase in the concentration of a particular downstream component in the signalling cascade (such as cAMP mentioned above) is ensured.

The parent cell line may additionally comprise a globin promoter and preferably also an enhancer, in particular LCR, arranged to enhance expression of a gene placed under the control of the globin promoter. A multiple cloning site is suitably provided adjacent the globin promoter such that various protein genes, and in particular receptor genes, may be introduced into the parent line as required.

Suitable parent cell lines may be obtained using empirical methods, for example by co-transforming cells with a vector including the reporter gene under the control of a response element and, for instance, a minimal globin promoter, and subjecting the cells to the target assay conditions and selected clones which produce the best signal (see Examples 7 and 8 hereinafter). An example of such a co-transformation system is the reporter cassette in the p3XVIP hyg (P) vector illustrated hereinafter, and a vector containing the LCR/globin gene promoter such as the pEV3 vector illustrated hereinafter.

In order to determine which clones have stably incorporated both vectors, each vector should contain a different selection marker gene, such as antibiotic resistance. For example, the p3XVIP hyg (P) vector includes a hygromycin resistance gene which confers resistance to hygromycin B, whilst the pEV3 vector includes a neomycin resistance gene which confers resistance to G418. The presence of this neomycin resistance gene in the parent cells hinders the transformation of this cell line with a vector allowing expression of an heterologous protein, when this protein is encoded by a gene cloned into a similar parent pEV3 vector.

Thus suitably other selection genes/chemical systems are utilised, e.g. a mammalian promoter, like the TK promoter in pEV3 (FIG. 1a), driving the expression of a Blasticidin-S deaminase enzyme (e.g. from the bsd gene of *Aspergillus terreus*), which is responsible for resistance to Blasticidin S.

Another way of obtaining such a parent cell line would be, for example to investigate the optimal organisation (distance, orientation etc.) of, say the LCR enhancer, such as the one in the pEV3 vector, and the reporter cassette, such as is carried by the p3XIP hyg (P) vector (and for this, the optimal clones selected using the above method would be useful) and reproduce this organisation in a single vector. This vector could then be utilised to assemble a parent cell line in MEL C88L or to co-transfect it with the expression vector. In yet a further alternative, the optimal organisation of enhancer/response element/minimal promoter/reporter gene can be identified (e.g. LCR/CRE (3xVIP)—βglobin minimal promoter—LacZ) and this could then be reproduced into a pEV3 like vector to provide both expression and reporter cassettes in the same vector.

The selection marker gene such as bsd as mentioned above, could either be incorporated into a single vector used to assemble the parent cell line, or it could be included in a vector used in co-transfection, such as new derivative of the pEV3 vector, pEV3/Blasto, where the neomycin resistance cassette is removed. The vector pEV3/Blasto could subsequently be utilised for expression of heterologous proteins affecting the cAMP signalling pathway, in a previously generated parent cell line where the expression of the reporter gene depends on an increase on the concentration of cAMP.

Use of a pre-characterised parent cell line is advantageous in that it harnesses the full benefits of using the LCR element to reduce numbers of clones which must be screened before "good expressers" are obtained. It would ensure that a clone with good inducibility of β-galactosidase expression as well as the capacity to express high levels of heterologous protein is obtained, even when only small numbers of clones (e.g. 6 clones/GPCR expression system) are characterised.

In the absence of a parent cell line of this type, generation of a cell line providing good expression levels of the GPCR receptor and a robustly and usefully inducible β-galactosidase reporter gene necessitates construction and analysis of a minimum of 25 to 50 clones because the reporter element is not itself associated with an LCR element. These numbers of clones are required to provide a reasonable chance of obtaining a clone that expresses a heterologous receptor at a suitable, together with the necessary inducibility of β-galactosidase expression.

In turn, the use of a parent cell line should also allow easier parallel assembly of cell lines expressing different GPCRs and/or different expression modules for the same GPCR. Higher productivity in useful cell line assembly can therefore be achieved.

A further major advantage of such a parent cell line is one of consistency: without it, from one transformation to the next it is impossible to obtain the same levels of inducibility of β-galactosidase expression because of more-or-less subtle position effects. A parent cell line avoids any difficulties in isolating a clone were the induction is robust enough to allow use of the cell line in high throughput screening assays. In turn, this reduces the amount of time necessary for characterising the clones obtained from a transformation, as well as the time necessary to develop a robust assay for high throughput screening. Consequently, by using a parent cell line the number of clones isolated from each transfection can be minimised, the consistency of β-galactosidase induction levels increased and the costs reduced.

Parent cell lines of this type form a further aspect of the invention.

The invention will now be particularly described by way of example with reference to the accompanying diagrammatic drawings in which:

FIG. 1a illustrates the expression vector pEV3 used as a recipient for the locust tyramine receptor (TyrLoc), such that the globin LCR enhancer and the murine β-globin promoter drive integration site independent expression of the receptor cDNA;

FIG. 1b illustates a reporter vector p3XVIP-hyg(P) which comprises three copies of a cAMP response element (3XVIP) upstream a minimal β-globin promoter arranged to drive the expression of a β-galactosidase reporter gene in the presence of cAMP in the cell;

FIG. 2 is a graph showing the dose-response relationship between tyramine (TA) concentration and $Ca^{2+}$ increase in MEL-TyrLoc cells compared to MEL C88L control cells which do not express the receptor;

Figure 8A:
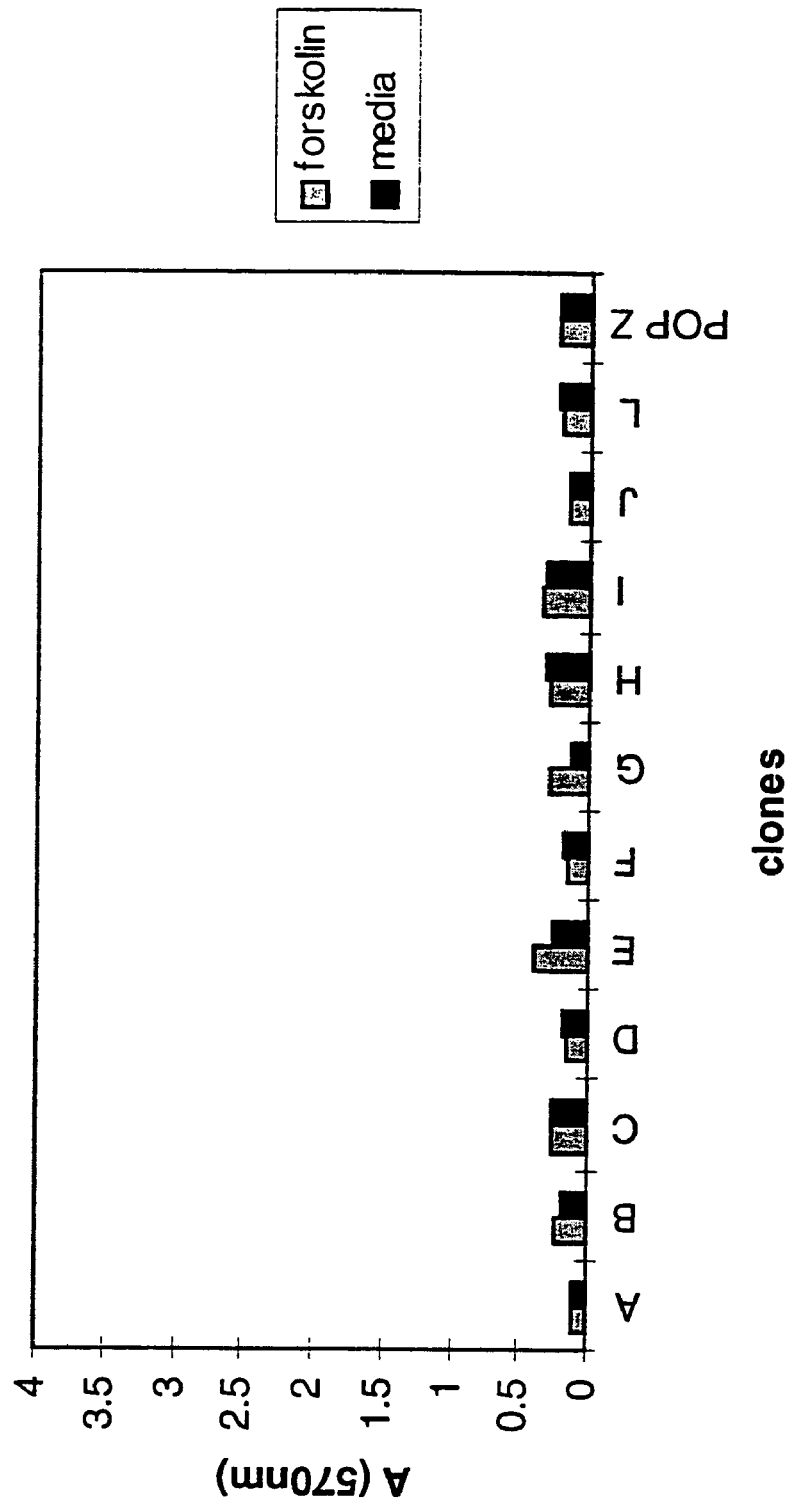
Figure 8B:
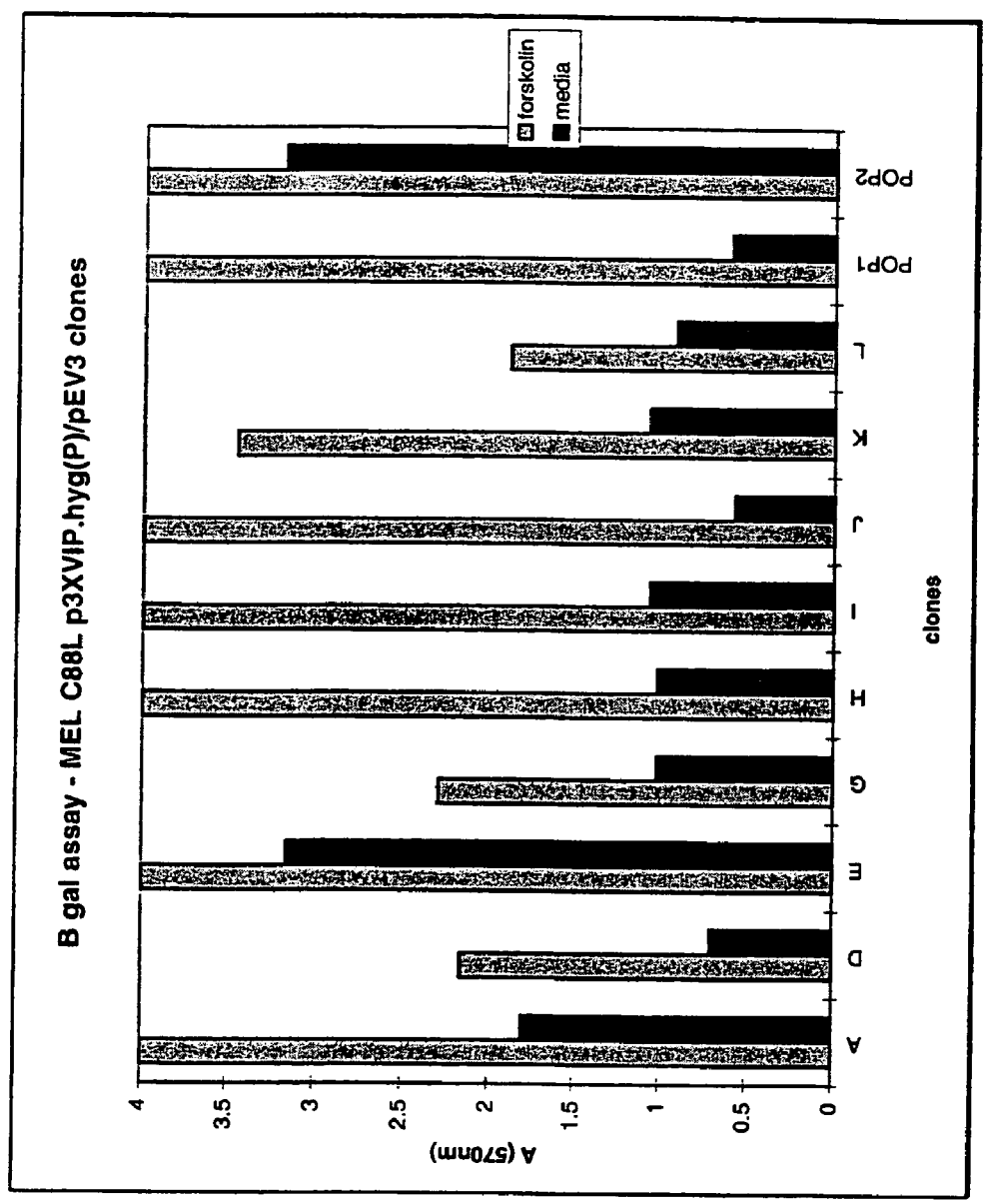

FIG. 8a illustrates the results obtained with a β-gal assay using MEL C88L cells transformed with the reporter vector p3XVIP hyg (P) where, in each group, the first column indicates cells incubated with 3.6 μM forskolin and the second shows those incubated in medium alone; and FIG. 8b illustrates the results obtained with a β-gal assay using MEL C88L cells co-transformed with the reporter vector p3XVIP hyg (P) and the expression vector pEV3 where, in each group, the first column indicates cells incubated with 3.6 μM forskolin and the second shows those incubated in medium alone.

EXAMPLE 1

Generation of the pEV3TyrLoc Expression Vector

The tyramine receptor cDNA from the locust *Locusta migratoria* was cloned into pEV3, downstream of the human globin locus control region (LCR) between the promoter and the second intron of the β-globin gene (FIG. 1a) as follows.

The coding region of the TyrLoc cDNA was amplified by polymerase chain reaction (PCR) from pVJ12 and pVJ12-IEG (J. Vanden Broek et al., J. Neurochemistry (1995) 64, 6, 2387–2395) using the following oligonucleotide primers:
5' PCR primer (TyrLocF2):
5'-TTTTAAGCTTGAATTCAGATCTGCCAC-
   CATGAACGGGTCTTCGGCTGC-3' (SEQ ID NO 1)
3' PCR primer (TyrLocRev):
5'-TTTTGGATCCGCGGCCGCGTCGACTCAT-
   GTCTTGAAGTGGAGCAGC-3' (SEQ ID NO 2)

The 5' primer contains the restriction sites Hind III, EcoR I and Bgl II, and the consensus translation enhancing sequence (GCCACC) (M. Kozak, J. Mol. Biol. (1987) 196 (4) 947–450). The 3' primer contains the restriction sites BamH I, Not I and Sal I. A PCR product was obtained with Pfu Polymerase (Stratagene) utilising the manufacturers protocol.

Figure 1A:
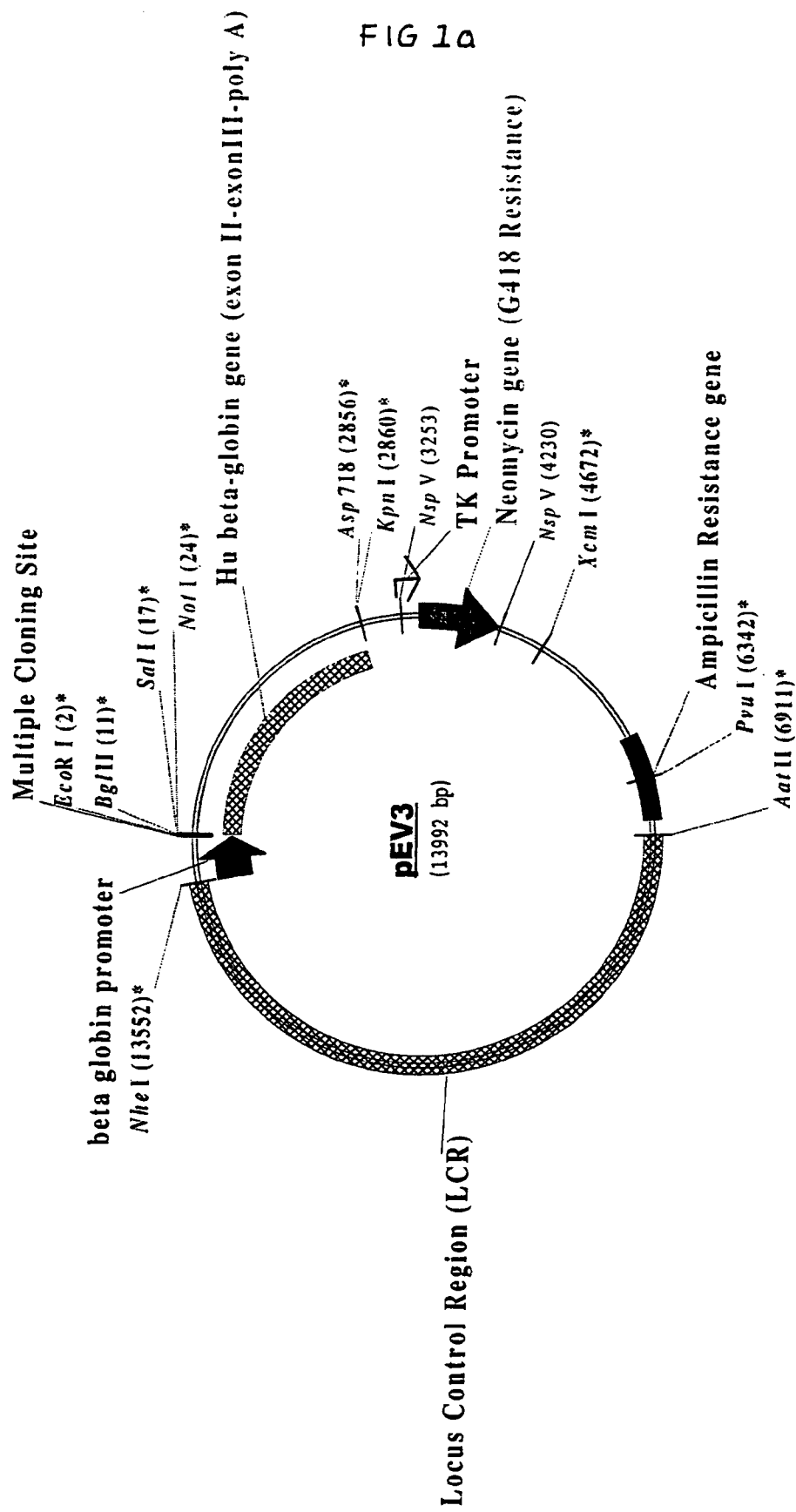

The following PCR conditions were used: 1 cycle of denaturation at 96° C. for 2 min followed by 40 cycles of denaturation at 96° C. for 1 min, annealing at 58° C. for 45 s and extension at 72° C. for 3 min; followed by a final extension reaction of 10 min at 72° C. The resulting PCR product was cloned into the pCR-Script (Amp SK+) vector (Stratagene) using the manufacturers protocol. Sequence analysis of a clone, confirmed the presence of a correctly edited insert. This insert was released from the pCR-Script (Amp SK+) background using EcoR I and Sal I enzymes (Pharmacia Biotech Products) and cloned by standard techniques into pEV3 digested with the same pair of enzymes (FIG. 1a).

The identity of the DNA utilised for MEL cell transformation was confirmed by restriction digestion and agarose gel electrophoresis and sequencing.

EXAMPLE 2

Cell Culture and Cell Transfections

Murine erythroleukemia C88 cells (Deisseroth A Hendrick D (1978) Cell 15 55–63) were cultured in Dulbecco's modified Eagle's medium (Gibco BRL) supplemented with 10% foetal bovine serum and 2 mM glutamine at 37° C., under 10% $CO_2$–90% air. "Leaky" MEL cells, C88L, which allow low level uninduced expression of globin genes in undifferentiated cells, were generated by prolonged culture of the cells (several months), prior to transfection studies.

The expression construct pEV3TyrLoc was introduced into leaky MEL-C88L cells by electroporation. Prior to transfection, 50 μg of pEV3TyrLoc were linearised at the unique Asp 718 site upstream of the neomycin cassette and downstream of the tyramine expression cassette. Transfection into the cell line MEL-C88L was performed by electroporation as described (Antoniou M (1991) "Induction of erythroid-specific expression in Murine Erythroleukemia (MEL) cell lines" in Methods in Molecular Biology Vol 7 Gene Transfer and Expression Protocols (eds Murray E J) 421434 The Humana Press Inc.).

After transfection, cells were diluted in culture medium to concentrations of about $10^4$, $10^5$ and $2 \times 10^5$ cells per ml and 1 ml aliquots were transferred to each well of a 24-well tissue culture plate (Gibco BRL-NUNC nunclon multidishes (polystyrene, radiation sterilised, with lids) 24 well plates, Cat # 143982A). Twenty four hours after the transfection, G418 was added to a concentration of 1 mg/ml in order to select for stable transfectants. Individual clones were picked, or pooled to generate populations, 7 to 10 days after the addition of selective medium.

For RNA purification and functionality studies, cells were maintained in exponential growth by passaging them every day for a period of 4 days (cells should increase from $2.10^5$ cells/ml to $6–8.10^5$ cells/ml in 24 hours when in log phase). For the RNA purification, one half of the cells was induced using 2% DMSO and incubated for a further period of 4 days.

EXAMPLE 3

RNA Analysis

Following induction with 2% DMSO, a Northern blot was performed on RNA extracted from induced and uninduced clones and populations. Approximately $1.10^7$ cells were washed with phosphate-buffered saline and resuspended in 1 ml of RNAzol B (Biogenesis). RNA was then purified according to the manufacturer's protocol. The RNA concentration was calculated from spectrophotometer readings at 260 nm.

Electrophoresis of the RNA samples (10 μg per lane) was performed through agarose gels containing 2.2 M formaldehyde in duplicate. The RNA was then transferred to a nylon membrane (Hybond-N, Amersham) in 20×SSC. After transfer, RNA was covalently cross-linked to the membrane by short-wave ultraviolet irradiation using a U.V. Stratalinker™ 2400 (Stratagene). Each duplicate membrane was prehybridised and hybridised (Church G M & Gilbert W (1984) Proc. Natl. Acad. Sci. USA 81 1991–1995; Feinberg A P and Vogelstein B (1983) Anal. Biochem. 132 6–13 (Addendum: Anal. Biochem. (1984) 137 266–267) using either $^{32}$P-labeled β-globin or $^{32}$P-TyrLoc-receptor probes.

There was a large increase in the production of TyrLoc mRNA after induction. Only clones that gave a strong signal on the Northern blot were used in further experiments.

EXAMPLE 4

Ca$^{2+}$ Measurements

Elevations in intracellular Ca$^{2+}$ in response to stimulation with ligands of the tyramine receptor were measured as follows. Since MEL cells loose the ability to signal on differentiation, and as receptor expression was readily detectable without induction of the MEL cells, uninduced MEL C88L cells of the invention were used.

Ca$^{2+}$ concentration was measured by using the acetoxymethyl (AM) ester of the fluorescent indicator fura-2 (Grynkiewicz G et al. (1985) J. Biol. Chem. 260 3440–3450). Cells were washed with NCF buffer (135 mM NaCl, 5 mM KCl, 6 mM glucose, 0.62 mM MgCl2.6H2O, 10 mM HEPES, pH 7.4 with 4 mM CaCl2) and resuspended at a concentration of $2.10^6$ cells/ml in NCF buffer containing 2 μM fura-2-AM (Molecular Probes). After 1 hour incubation in the dark at 27° C., the cell suspension was subjected to centrifugation at 1200 rpm for 5 minutes, resuspended in an equal volume of NCF buffer and incubated for an additional 30 min in the dark. Aliquots were centrifuged as above and resuspended in 3 ml NCF buffer. Measurements of intracellular calcium were made fluorimetrically in a LS-50B Luminescence Spectrophotometer (Perkin-Elmer) in the presence and absence of the appropriate test chemical. Excitation wavelength alternated between 340 and 380 nm. The fluorescence intensity was monitored at an emission wavelength of 510 nm.

The different clones were tested in order to see whether there was a difference in their functional response to 10 μM tyramine (TA), an endogenous insect neurotransmitter. All of the clones tested gave a similar response (data not shown), therefore only one clone was used in further experiments. FIG. 2 shows a dose-response experiment for this clone: there was a clear transient increase in Ca$^{2+}$ after addition of TA. The lowest concentration of TA tested was 0.01 μM. A maximal response was obtained when using 1 μM TA. Untransformed MEL-C88L cells gave no response with concentrations as high as 100 μM TA.

Addition of ionomycin (2 μM), a Ca$^{2+}$-ionophore, to the cells resulted in a large increase of the intracellular Ca$^{2+}$ concentration, showing that the cells were loaded with suitable levels of fura-2. The Ca$^{2+}$ dependency of the TA response was tested by using NCF buffers with different Ca$^{2+}$ concentrations. In low Ca$^{2+}$ buffer (no extra Ca$^{2+}$ added to the buffer), the elevated Ca$^{2+}$ level quickly dropped down to its initial concentration. Also, the Ca$^{2+}$ release seen in the presence of low Ca$^{2+}$ buffer was greater than the release seen in high Ca$^{2+}$ buffer (4 mM Ca$^{2+}$) (data not shown).

These observations and results are consistent with the expectation that the initial cytoplasmic Ca$^{2+}$ increase comes from the release of the internal stores, whilst a sustained Ca$^{2+}$ level is achieved by an influx of Ca$^{2+}$ from the outside of the cell. The cytosolic Ca$^{2+}$ concentrations are probably lower in low Ca$^{2+}$ buffer due to establishment of an equilibrium across the cell membrane. This is the reason why the fura-2 340 nm/380 nm fluorescence ratio increases more in low Ca$^{2+}$ buffer, i.e. there was initially more free fura-2 compared to cells in high Ca$^{2+}$ buffer.

Figure 3:
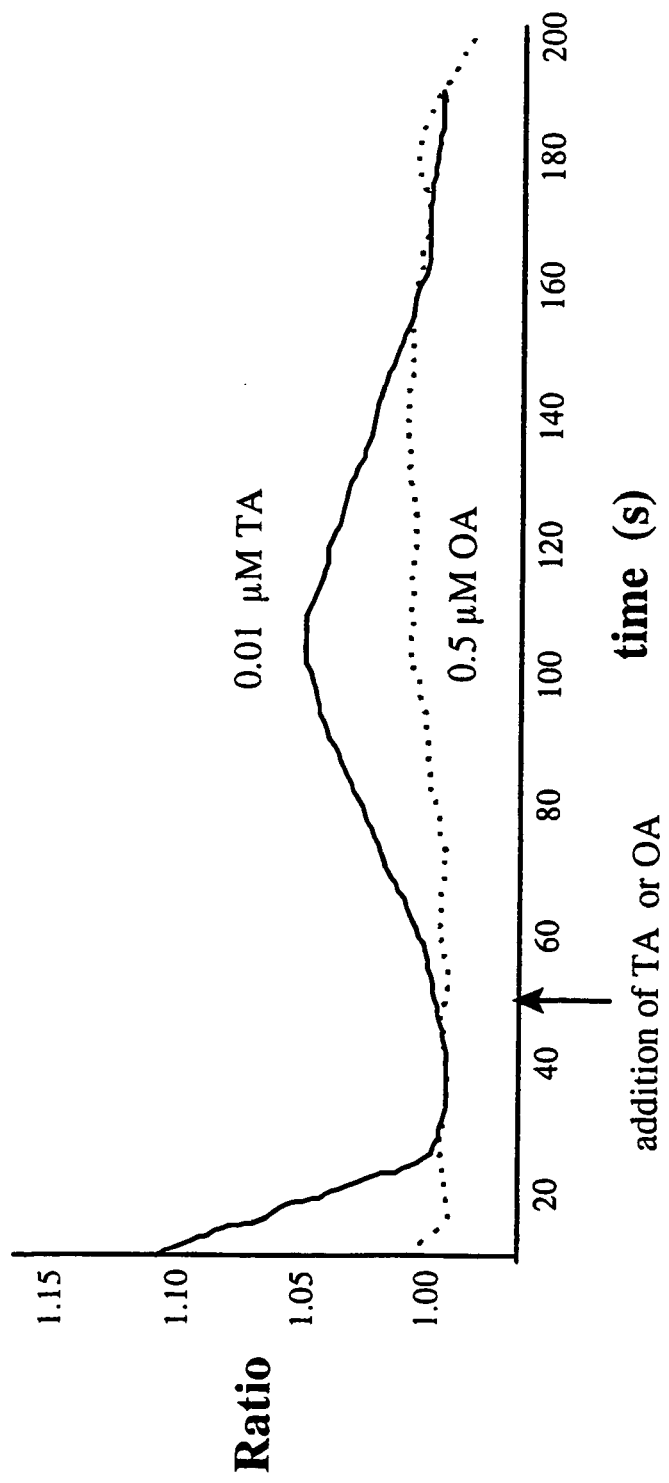
FIG. 3 is a graph showing a comparison of calcium responses in MEL-TyrLoc cells elicited by tyramine (TA) (10 nM) and octopamine (OA) (0.5 µM)

The effect of different agonists and antagonists of the tyramine receptor was investigated. The response to octopamine (OA) was measured, since OA is a phenolamine which is structurally related to TA. Though it was used at a 50 times higher concentration, OA increased the Ca$^{2+}$ concentration to a much lesser extent than TA, showing the specificity of the receptor for TA (FIG. 3).

At concentrations below 20 μM, metaclopramide had no detectable effect on basal Ca$^{2+}$ concentrations or on the response of the cells to TA. Chlorpromazine and mianserin clearly inhibited the Ca$^{2+}$ increase induced by TA. Both naphazoline and tolazoline were weak antagonists (data not shown).

Figure 4:
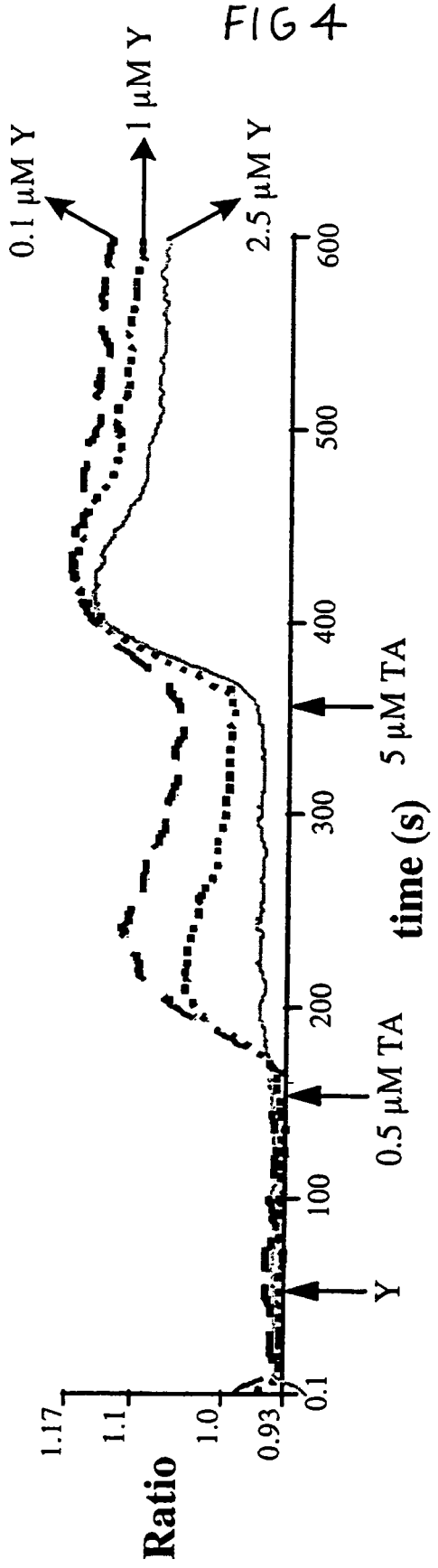
FIG. 4 is a graph illustrating that the addition of different concentrations of yohimbin (Y) results in an inhibition of the response to 0.5 μM TA, but could not inhibit the response to high TA concentrations (5 μM)

Yohimbine proved to be the strongest antagonist of the substances which were tested and a dose-response assay was performed (FIG. 4). Yohimbine was added after 50 s at different concentrations (0.1, 1 and 2.5 μM). Subsequently, 0.5 μM and 5 μM of TA was added after 150 and 350 s respectively. Yohimbine produced a concentration-dependent inhibition of the response to 0.5 μM TA, but it could not inhibit the 5 μM TA response, within the concentration range employed.

EXAMPLE 5 cAMP Measurements

The effect of TA on the cAMP level of the transformed and untransformed cells was investigated. MEL-C88L and MEL-TyrLoc cells were seeded in 6-well plates to a density of $8.10^5$ cells/well and allowed to attach. The cell medium was removed and, in different wells, replaced with different NCF buffer solutions as follows:

(i) NCF+1 μM tyramine (TA),
(ii) NCF+10 μM forskolin (Fsk),
(iii) NCF+10 μM Fsk+1 nM to 10 μM TA.

where NCF comprised 135 mM NaCl, 5 mM KCl, 6 mM glucose, 0.62 mM MgCl$_2$, 10 mM Hepes pH 7.4 4 mM CaCl$_2$.

For the use of other ligands than TA, the solutions were:

(iv) NCF+10 μM Fsk+1 μM OA,
(v) NCF+10 μM Fsk+0.1 μM TA+100 nM to 1 nM yohimbine,
(vi) NCF+10 μM Fsk+0.1 μM TA+10 nM mianserin; and
(vii) NCF+10 μM Fsk+0.1 μM TA+10 nM chlorpromazine.

All solutions contained 200 μM 3-iso-1-butylmethylxanthine (IBMX) in order to inhibit cAMP phosphodiesterase. In each study, triplicate wells were incubated with the same solution at 37° C. for exactly 30 min.

In order to extract the cAMP, 100% ice-cold ethanol was added to each well to a final concentration of 65%. After 5 min incubation at room temperature, the solution was removed from the wells which were then rinsed with 65% ethanol. The eluates from the same well were then pooled together and evaporated using a speedvac. cAMP was then measured using the Scintillation Proximity Assay (Amersham), according to the manufacturers recommended procedure. This experiment was done in triplicate.

Figure 5:
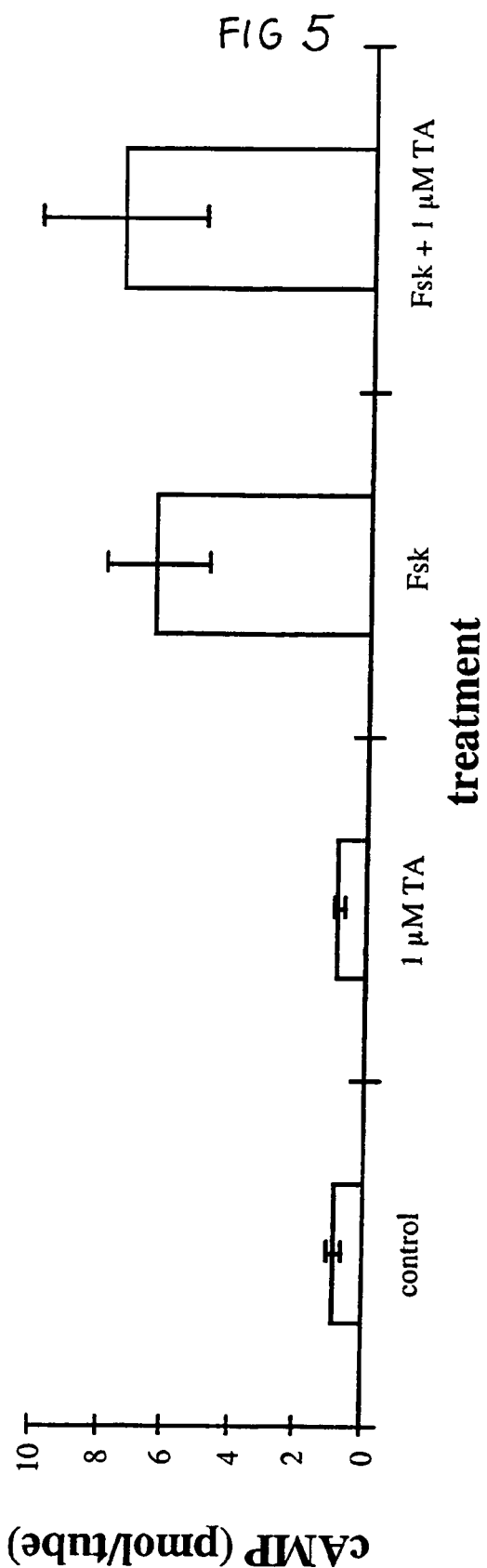
FIG. 5 is a graph showing control cAMP measurements of untransformed MEL-C88L cells in the presence of forskolin (FSK)

FIG. 5 shows the cAMP levels in untransformed MEL-C88L cells: addition of 1 μM TA did not result in any effect. Forskolin, with or without TA, increased the cAMP level more than 6 times.

Figure 6:
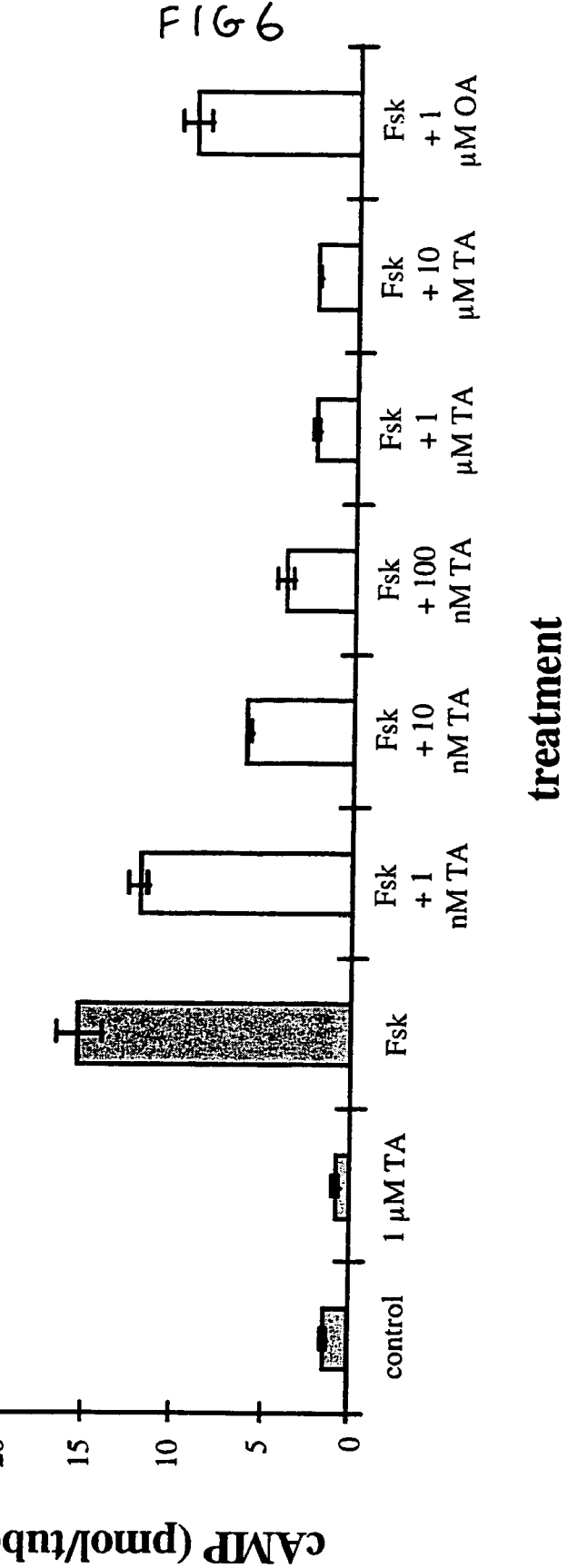
FIG. 6 illustrates the inhibition of forskolin induced increase of cAMP by tyramine in MEL-TyrLoc cells.

FIG. 6 shows the effect of TA on MEL-TyrLoc cells: TA significantly inhibits the forskolin-induced increase of cAMP. This response was dose-dependent; a minimal and maximal response was achieved when using 1 nM TA and 1 μM TA respectively. There was a 4-fold decrease in cAMP production with 1 μM TA when compared to 1 μM OA, therefore, indicating that TA is a much stronger inhibitor of cAMP production in these cells.

Yohimbine inhibited the effect of TA in a dose dependent manner. The antagonistic effects of mianserin and chlorpromazine were also confirmed (data not shown).

The measurements were found to be highly reproducible.

EXAMPLE 6

β-Galactosidase Assay Using Dopamine Clones

MEL C88L cells were transformed with the serotonin and dopamine receptors using conventional methods and from northern blot analysis, 5–6 clones were chosen for further evaluation.

Generation of pEV3D-Dop1 Expression Vector

The Dopamine Receptor cDNA from the fruit fly *Drosophila melanogaster* was cloned into pEV3, downstream of the human globin locus control region (LCR) between the promoter and the second intron of the β-globin gene (FIG. 1a) as follows.

The coding region of the D-Dop1 cDNA was amplified by PCR from pDMdop1 (pDMdop1 contains a D-Dop1 cDNA as a partial EcoRIdigest from pcDNAI construct cloned into pBluescrip SK vector). (F. Gotzes et al, Receptors on Channels (1994) 2, 131–141).

The amplification was performed using the following oligonucleotide primers:
5' PCR primer (Dop D1/5 FR);
5'-TTTT AAGCTT AGATCT GCCACC ATG TAC ACA CCA ACA CCC ATTT G-3' (SEQ IS NO 3)
3' PCR primer (Dop D1/5 RV);
5'-TTTT GC GG CC GC GTC GAC TCA AAT CGC AGACACCTGCTC-3' (SEQ ID NO 4)

The 5' primer contains the restriction sides HindIII, and BglII and the consensus translation enhancing sequence (GCC ACC) (M. Kozak, 1987 supra). The 3' primer contains the restriction sites Not I and Sal I. A PCR product was obtained with Pfu Polymerase (Stratagene) utilising the manufacturers protocol.

The following PCR conditions were used: 1 cycle of denaturation at 96° C. for 2 min followed by 35 cycles of denaturation at 96° C. for 1 min, annealing at 57° C. and 60° C. for 45 s and extension at 72° C. for 3 min; followed by a final extension reaction of 10 min at 72° C. The resulting PCR product was cloned into the PCR-script (Amp SK+) vector (stratagene) using the manufacturers protocol. Sequence analysis of a clone, confirmed the presence of a correctly edited insert. This insert was released from the PCR-Script (AMP SK+) background using BglII and NotI enzymes (Pharmacia Biotech Products) and cloned into pEV3 (FIG. 1a).

The identity of the DNA utilised for Mel cell transformation was confirmed by restriction digestion and agarose gel electrophoresis and sequencing.

Cell Culture and Cell Transfection

Murine erythroleukemia C88L were cultured as described in Example 2.

Figure 1B:
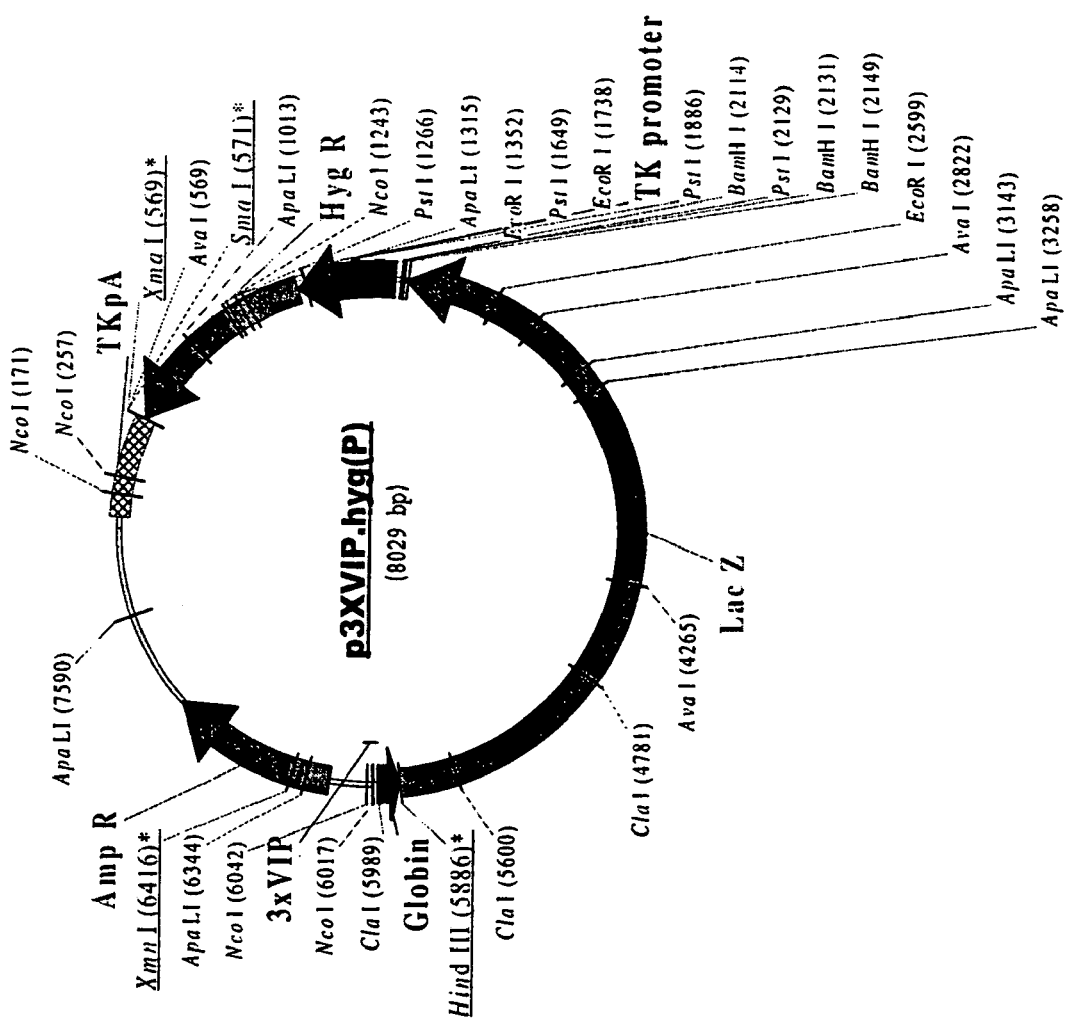

The expression construct pEV3D-Dop 1 and the reporter construct p3XVIP Ryg(P) See FIG. 1b) were co-transformed into Mel-C88L cells by electroporation. Prior to transfection, 30 μg of pEV3D-Dop1 and 30 μg of p3XVIP hyg (P) were linearised respectively at the unique sites Asp 718 and XmnI.

The unique Asp718 site in the pEV3D-Dop1 vector is found upstream of the neomycin cassette and downstream of the dopamine expression cassette. The unique XmnI site in the p3XVIP hyg (P) vector is found in the ampicillin gene and is flanked by both the reporter expression cassette and the hygromycin cassette. Transfection into the cell line Mel-C88L was performed by electroporation as described (M. Antoniou, 1991 supra). After transfection, cells were diluted in culture medium to concentrations of about $10^4$, $10^5$ and $2 \times 10^5$ cells per ml and 1 ml aliquots were transferred to each well of a 24-well tissue culture plate (reference as in example 2). Twenty four hours after the transfection, G418 was added to a concentration of 1 mg/ml in order to select for stable transfectants which would contain either the pEV3 D-Dop1 expression construct on its own or with the reporter vector p3XVIP hyg (P). Individual clones were picked, or pooled to generate populations, 7 to 10 days after the addition of selective medium.

These clones and populations were visually assessed as being dividing vigorously before being passaged into media containing two selection agents: G418 and hygromycin B at respective concentrations of 1 mg/ml and 0.8 mg/ml. This was done in order to select only for transfectants having stably integrated both vectors: pEV3D-Dop I and p3XVIP.hyg(P).

For RNA purification, cells were maintained in exponential growth by passaging them every day for a period of 4 days (cells should increase from $2 \times 10^5$ cells/ml to $6$–$8 \times 10^5$ cells/ml in 24 hours when in log phase). One half of the cells was then induced using 2% DMSO and incubated for a further period of 4 days. RNA analysis was carried out as described in Example 3.

β-Galactosidase Assays Using Dopamine Clones 6 dopamine clones were washed in phenol red free RPMI media (GIBCO) containing 5% FCS and 1% glutamine and resuspended at concentrations of $1.25 \times 10^7$ cells/ml and $2.5 \times 10^6$ cells/ml. These cells were then transferred to 96-well microtitre plates a final concentrations of $2 \times 10^5$ cells/well and $1 \times 10^6$ cells/well. Additions of either a) Forskolin (3 μM) or b) Dopamine (agonist) 10 μM or c) Media were made at each of the cell concentrations. 2 replicates/clone/concentrations were set up.

After incubation for 5 hours at 37° C. in an atmosphere of 10% $CO_2$, a chlorophenol red β-D-galactopyranoside (CPRG) solution was added. The solution comprised 11.4 mg CPRG (Boehringer), 500 μl 10× Z buffer, 75 μl 20% SDS, 5 ml $H_2O$ and 7 μl ercaptoethanol. 10× Z buffer consists of 0.47M $Na_2HPO_4(2H_2O)$, 0.4M $NaH_2PO_4$ $(2H_2O)$, 0.1M KCl, 10 mM $MgSO_4(7H_2O)$, adjusted to pH 7.0 with NaOH solution.

Figure 7:
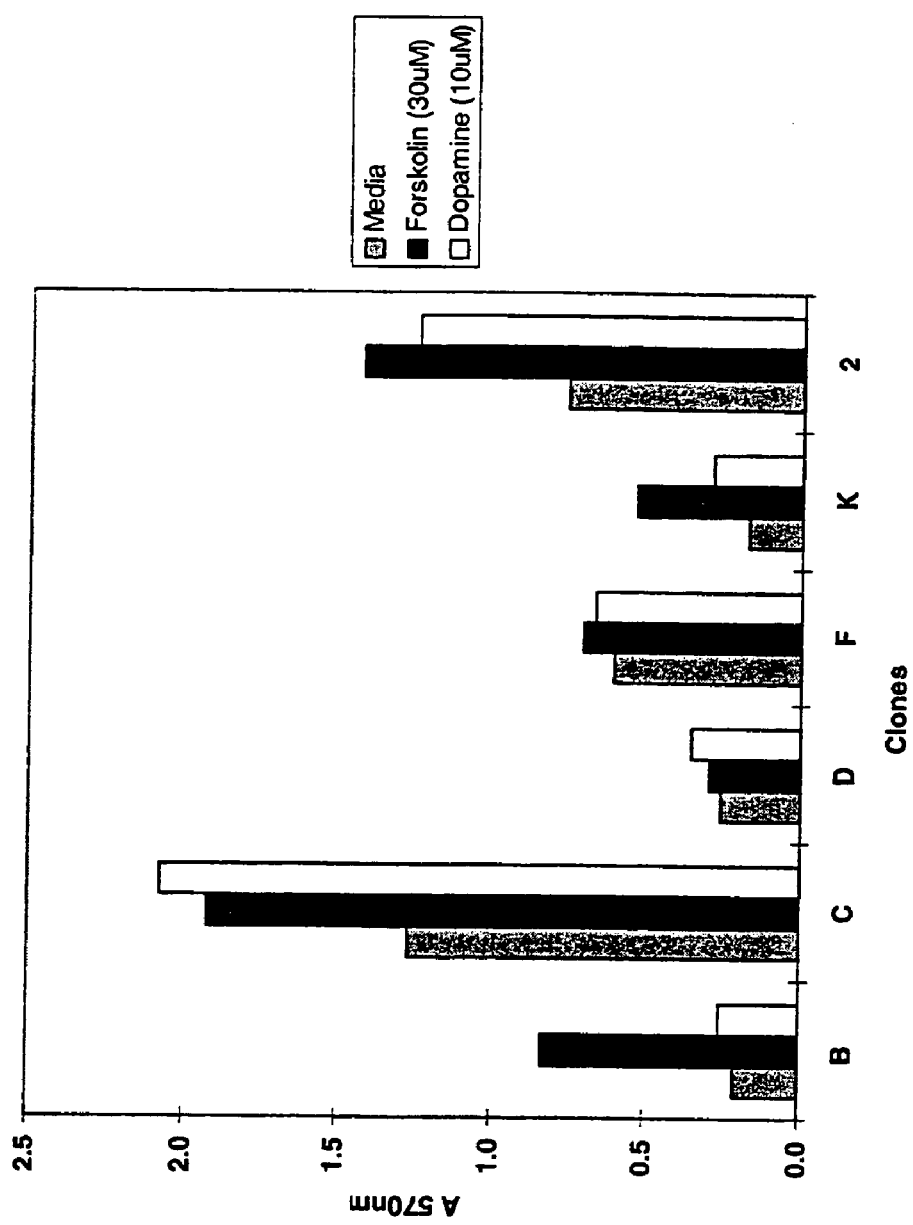
FIG. 7 illustrates the results obtained with a β-gal assay using MEL cells transformed with a dopamine receptor and the reporter vector where, in each group, the first column indicates cells incubated in medium alone, the second shows those incubated with 3 μM forskolin, the third column shows the results of incubation with 10 μM dopamine.

Plates were then incubated overnight under the same conditions and the absorbance at 570 nm determined using a spectrophotometer (MRX Microplate Reader (Dynatech Laboratories). Results for the dopamine clones at a concentration of $1 \times 10^6$ cells/well are shown in FIG. 7. Clones C and 2 showed an increase in absorbance at 570 nm, indicating an increase in cyclic AMP, both in the presence of forskolin and in the presence of dopamine. This signal may be useful in detecting agonists and antagonists of the dopamine receptor.

The serotonin clones showed a similar increase in cyclic AMP in the presence of forskolin. In the presence of serotonin no effect was seen but in the presence of forskolin and serotonin a decrease in forskolin stimulated cAMP was observed. This signal may be useful in detecting agonists and antagonists of the serotonin receptor.

EXAMPLE 7

Generation of Control MEL C88L Reporter Clones Expressing no Receptor

Cell Culture and Cell Transfection

Murine erythroleukemia C88 "leaky" (Deisseroth A, 1978 supra) were cultured as in Example 2.

The reporter construct p3XVIP hyg(P) (FIG. 1b) was transformed into Mel-C88L cells by electroporation, either on its own (Transfection 1) or in parallel with the expression vector pEV3 (FIG. 1a) (Transfection 2). Prior to transfection, 30 μg of pEV3 and 60 μg of p3XVIP hyg (P) were linearised respectively at the unique sites Asp 718 and XmnI.

The unique Asp718 site in the pEV3 vector lies upstream of the neomycin cassette and downstream of the empty expression cassette containing the LCR enhancer. The unique XmnI site in the p3XVIP hyg (P) vector is found in the ampicillin gene and is flanked by both the reporter expression cassette and the hygromycin cassette. Transfections into the cell line Mel-C88L were performed by electroporation as described (M. Antoniou, 1991 supra). After each transfection, cells were diluted in culture medium to concentrations of about $10^4$, $10^5$ and $2 \times 10^5$ cells per ml and 1 ml aliquots were transferred to each well of a 24-well tissue culture plate (reference as in example 2). Twenty four hours after the transfection,: hygromycin B (at a concentration of 0.8 mg/ml for Transfection 1) or G418 and hygromycin B (at respective concentrations of 1 mg/ml and 0.8 mg/ml for Transfection 2) were added in the transformations in order to select for stable transfectants which would either contain the reporter vector p3XVIP hyg (P) on its own (Transfection 1) or under the influence of the LCR enhancer from the expression vector pEV3 (Transfection 2). In Transfection 2 the double selection would select for clones containing both vectors. Individual clones were picked, or pooled to generate populations, 7 to 10 days after the addition of selective medium.

For RNA purification, cells were maintained in exponential growth by passaging them every day for a period of 4 days (cells should increase from $2 \times 10^5$ cells/ml to $6-8 \times 10^5$ cells/ml in 24 hours when in log phase). One half of the cells for each clone or population was then induced using 2% DMSO and incubated for a further period of 4 days. RNA analysis was carried out as described in Example 3.

β-Galactosidase Assays Using p3XVIP.hyg(P) or p3XVIP.hyg(P)/pEV3 Clones 12 clones and 2 populations were tested from each of Transfection 1 and 2. These clones and populations were washed in phenol red free RPMI media (GIBCO) containing 5% FCS and 1% glutamine and resuspended at an estimated concentration of between 1 and $4 \times 10^6$ cells/ml. These cells were then transferred to 96-well microtitre plates at an estimated final concentration of between 1 to $4 \times 10^5$ cells/well. Additions of either a) Forskolin (3.6 μM) or b) Media were made to the cells. 2 replicates/clone/concentrations were set up.

After incubation for 6 hours at 37° C. in an atmosphere of 10% $CO_2$, a chlorophenol red β-D-galactopyranoside (CPRG) solution was added. This solution comprised 11.4 mg CPRG (Boehringer), 500 μl 10× Z buffer, 75 μl 20% SDS, 5 ml $H_2O$ and 7 μl ercaptoethanol. 10× Z buffer consists of 0.47M $Na_2HPO_4(2H_2O)$, 0.4M $NaH_2PO_4$ $(2H_2O)$, 0.1M KCI, 10 mM $MgSO_4(7H_2O)$, adjusted to pH 7.0 with NaOH solution.

Plates were then incubated overnight under the same conditions and the absorbance at 570 nm determined using a spectrophotometer (MRX Microplate Reader—Dynatech Laboratories). Results for the p3XVIP.hyg(P) and p3XVIP.hyg(P)/pEV3 clones and populations are shown in FIGS. 8a and 8b respectively.

The p3XVIP.hyg(P) clones and population showed no significant increase in absorbance at 570 nm either in the presence or absence of forskolin: this indicates that there is no significant increase of α-galactosidase expression. This expression would have indicated an increase in cyclic AMP concentration in the cells, in turn caused by the presence of forskolin. In contrast, the p3XVIP.hyg(P)/pEV3 clones and populations showed a variety of results ranging from no significant increase in 570 nm absorbance (Clones B and F—data not shown) to near constitutive expression (Clone E and Population Pop2—see FIG. 8b) or very good inducibility of β-galactosidase expression caused by the increase of cAMP concentration in the cells in the presence of forskolin (p3XVIP.hyg(P)/pEV3 clone J and Pop1—see FIG. 8b).

This shows that both vectors are necessary for full inducibility of β-galactosidase expression by the increase of cAMP concentration in the cells. Variability in the inducibility of β-galactosidase expression between different clones is probably due to the distance, in the genome of the cell, between the LCR enhancer (pEV3; FIG. 1a) and the {CRE (3xVIP)—β globin minimal promoter} which drives the expression of the LacZ gene (p3XVIP.hyg(P); FIG. 1b). The optimal distance seems to have been reached in clone J (FIG. 8b). This cell line can be used as a control in experiments were MEL C88L cells have been transformed with p3XVIP.hyg(P) and pEV3 expressing a heterologous protein affecting the cAMP signalling pathway.

EXAMPLE 8

Generation of a Parent MEL C88L {p3XVIP.hyg(P)/LCR} Cell Line

The experiment reported in example 7 suggested the utility in assembly of a parent cell line containing the p3XVIP.hyg(P) vector at a suitable distance from the LCR enhancer contained in pEV3. This parent cell line clone would, like p3XVIP.hyg(P)/pEV3 clone J, have easily demonstrated inducibility of β-galactosidase expression by an increase of the cAMP concentration in the cells. However, p3XVIP.hyg(P)/pEV3 clone J could not itself be utilised as parent cell line because it already contained a standard pEV3 carrying the neomycin resistance gene (and hence confering resistance to G418). The presence of this resistance gene in the parent cells hinders the transformation of this cell line with a vector allowing expression of an heterologous protein, when this protein is encoded by a gene cloned into the parent pEV3 vector. The following description details-one way of obtaining a suitable parent cell line.

Generation a ΔNeomycin pEV3 Vector

In this example, the pEV3 vector was be modified to remove the neomycin gene which confers G418 resistance. Specifically the neomycin expression cassette (TK promoter—neomycin gene—FIG. 1a) was removed from the pEV3 vector using KpnI and NspV enzymes (Amersham Pharmacia Biotech), generating the vector ΔNeomycin pEV3.

Cell Culture and Cell Transfection

Murine erythroleukemia C88 "leaky" (Deisseroth A, 1978 supra) were cultured as in Example 2.

The reporter construct p3XVIP hyg(P) (FIG. 1b) was then co-transformed with the vector ΔNeomycin pEV3 into Mel-C88L cells by electroporation. Prior to transfection, 30 μg of ΔNeomycin pEV3 and 30 μg of p3XVIP hyg (P) were linearised respectively at the unique sites Asp 718 and XmnI.

The unique Asp718 site in the pEV3 vector lies downstream of the empty expression cassette containing the LCR enhancer. The unique XmnI site in p3XVIP hyg (P) vector is found in the ampicillin gene and is flanked by both the reporter expression cassette and the hygromycin cassette. Transfections into the cell line Mel-C88L were performed by electroporation as described (M. Antoniou, 1991 supra). After each transfection, cells are diluted in culture medium to concentrations of about $10^4$, $10^5$ and $2\times10^5$ cells per ml and 1 ml aliquots transferred to each well of a 24-well tissue culture plate (reference as in example 2). Twenty four hours after the transfection, hygromycin B (at a concentration of 0.8 mg/ml) was added in the transformation in order to select for stable transfectants which would either contain the reporter vector p3XVIP hyg (P) on its own or under the influence of the ΔNeomycin pEV3 vector's LCR enhancer (it was not be possible to select for the double transformants directly as the ΔNeomycin pEV3 vector does not contain any markers allowing selection in mammalian cells). Individual clones were picked, or pooled to generate populations, 7 to 10 days after the addition of selective media.

For RNA purification, cells were maintained in exponential growth by passaging every day for a period of 4 days (cells grow from $2\times10^5$ cells/ml to $6-8\times10^5$ cells/ml in 24 hours when in log phase). One half of the cells for each clone or population was then induced using 2% DMSO and incubated for a further period of 4 days. RNA analysis was carried out as described in Example 3.

β-Galactosidase Assays Using p3XVIP.hyg(P) or p3XVIP.hyg(P)/ΔNeomycin pEV3 Clones 50 clones and 2 populations were tested for inducibility of β-galactosidase expression by the increase of cAMP concentration in the cells. The clones and populations were washed in phenol red free RPMI media (GIBCO) containing 5% FCS and 1% glutamine and then resuspended at a concentration of between 1 and $4\times10^6$ cells/ml. Cell suspensions were then transferred to 96-well microtitre plates at a final concentration of between 1 to $4\times10^5$ cells/well. Additions of either a) Forskolin (3 to 3.6 μM) or b) Media were made to the cells. 2 replicates/clone/concentrations were set up.

After incubation for 5 to 6 hours at 37° C. in an atmosphere of 10% $CO_2$, a chlorophenol red β-D-galactopyranoside (CPRG) solution was added. This solution comprised 11.4 mg CPRG (Boehringer), 500 μl 10× Z buffer, 75 μl 20% SDS, 5 ml $H_2O$ and 7 μl mercaptoethanol. 10× Z buffer consists of 0.47M $Na_2HPO_4(2H_2O)$, 0.4M $NaH_2PO_4$ $(2H_2O)$, 0.1M KCl, 10 mM $MgSO_4(7H_2O)$, adjusted to pH 7.0 with NaOH solution.

Plates were incubated overnight under the same conditions and the absorbance at 570 nm was determined using a spectrophotometer (MRX Microplate Reader—Dynatech Laboratories). The results from this experiment were similar to those obtained in example 7, with a mixture of cells responding either like Transfection 1 or 2 clones. This is due to the fact that in this transfection, there were a mixture of clones produced and containing either p3XVIP hyg(P) vector on its own or co-integrated with ΔNeomycin pEV3 vector, because of the simple selection with hygromycin. A parent MEL C88L {p3XVIP.hyg(P)/LCR} cell line was then selected on the basis of criteria including optimal inducibility of β-galactosidase expression by the increase of cAMP concentration in the cells, as for p3XVIP.hyg(P)/pEV3 clone J.

Other modifications of the present invention will be apparent to those skilled in the art without departing from the scope of the invention.

The invention claimed is:

1. An isolated erythroid cell as deposited at the European Collection of Cell Cultures under Accession number 99012801.

2. The isolate erythroid cell according to claim 1 which is transformed with a vector comprising a sequence which encodes a tyramine receptor under the control of a globin promoter.

3. The isolated erythroid cell according to claim 2 which has been further transformed such that it contains a globin promoter associated with a reporter cassette containing a β-galactosidase gene under the control of a response element susceptible to modulation by a signalling cascade of said cell.

4. The isolated erythroid cell according to claim 3 wherein said response element is the Locus control Region (LCR) enhancer, wherein said enhancer is at an optimal distance of said reporter cassette such that the expression of the β-galactosidase gene is dependent on the concentration of a downstream component in the signaling cascade.

5. A method for detecting whether a tyramine receptor binds to a G-protein and triggers an endogenous signaling cascade of an erythroid cell comprising the steps of: providing the erythroid cell according to claim 3 or 4, incubating the cell in the presence of a ligand capable of binding the tyramine receptor, measuring the expression levels of the β-galactosidase gene, comparing the β-galactosidase expression levels with those of an untransformed erythroid cell, and detecting the binding of a tyramine receptor to a G-protein by observing a difference between the levels of β-galactosidase expression from transformed and untransformed erythroid cells.

6. The method of claim 5, wherein the ligand is an agonist or antagonist and the incubation is performed either (I) in (a) the presence and (b) the absence of a potential agonist of the tyramine receptor and/or (II) in the presence of a known agonist and (a) the presence or (b) the absence of a potential antagonist of the tyramine receptor; and measuring and comparing the levels of cyclic AMP or calcium ion of (Ia) and (Ib) and/or (IIa) and (IIb).

7. A method for detecting whether a tyramine receptor binds to a G-protein and triggers an endogenous G-protein coupled signaling cascade of an erythroid cell comprising the steps of; transforming an erythroid cell according to claim 6 with a vector comprising a sequence which encodes a tyramine receptor under the control of a globin promoter, incubating the cell with a ligand capable of binding the tyramine receptor, measuring the cyclic AMP levels or free calcium ion concentration within the cell, comparing the cyclic AMP levels or the free calcium ion concentration with that of an untransformed erythroid cell, and detecting the tyramine receptor binding to a G-protein by observing a difference in the cyclic AMP levels or calcium ion concentrations measured between the transformed and untransformed erythroid cells.

8. The method according to claim 1 wherein the calcium levels are measured by means of a fluorescent indicator.

9. The method of claim 1, wherein the ligand is an agonist or antagonist and the incubation is performed either (I) in (a) the presence and (b) the absence of a potential agonist of the tyramine receptor and/or (II) in the presence of a known agonist and (a) the presence or (b) the absence of a potential antagonist of the tyramine receptor; and measuring and comparing the levels of cyclic AMP or calcium ion of (Ia) and (Ib) and/or (IIa) and (IIb).

* * * * *